United States Patent [19]
Dehner

[11] Patent Number: 5,574,763
[45] Date of Patent: Nov. 12, 1996

[54] COMPUTED TOMOGRAPHY APPARATUS

[75] Inventor: Guenter Dehner, Erlangen, Germany

[73] Assignee: Siemens Aktiengesellschaft, Munich, Germany

[21] Appl. No.: 381,711

[22] Filed: Jan. 31, 1995

[30] Foreign Application Priority Data

Feb. 21, 1994 [DE] Germany ............................ 44 05 505.6

[51] Int. Cl.⁶ ................................................... H05G 1/06
[52] U.S. Cl. ................................ 378/17; 378/20; 378/195
[58] Field of Search ..................................... 378/17, 4, 20, 378/193, 195, 196, 197, 198, 208, 209

[56] References Cited

U.S. PATENT DOCUMENTS 3,927,326  12/1975  Kunne et al. ............................ 378/179
4,961,208  10/1990  Okada ........................................ 378/20

FOREIGN PATENT DOCUMENTS 0495137  7/1992  European Pat. Off. .
8317036  10/1983  Germany .

*Primary Examiner*—Don Wong
*Attorney, Agent, or Firm*—Hill, Steadman & Simpson

[57] ABSTRACT

A computed tomography apparatus is described which enables an optimum examination of the small intestine region, having a patient support which permits a scan to be conducted of a patient with the patient in a substantially upright, but slightly tilted, position, and a control unit for maintain the gantry containing the x-ray source and detector at the same angle relative to said patient support for all positions of the patient support during a scan. A three-dimensional image reconstruction ensues such that, given a contrast agent fill of hollow organs, the hollow organ is computationally sliced, a contrast agent trunk is computationally removed and the inside of the hollow organ is thus displayed. The hollow organ can be displayed sliced in side-by-side images but can also be displayed in the form of an involution of its inside view.

10 Claims, 9 Drawing Sheets

COMPUTED TOMOGRAPHY APPARATUS

BACKGROUND OF THE INVENTION

1. Field of the Invention

The present invention is directed to a computed tomography apparatus, and in particular to a computed tomography apparatus which permits examinations in the area of the small intestine to be conducted with improved visual definition in the image.

2. Description of the Prior Art

Computed tomography is currently the suitable method for radiological examination for many objectives. In addition to the display of bone structures, a good presentation of soft body parts is possible. Vessels can be particularly emphasized by the intravenous administration of contrast agents. The various known post-processing possibilities provide additional information for the diagnosis.

A good and radiation-free finding with respect to the esophagus and stomach is currently possible in the region of the gastrointestinal tract on the basis of gastroscopy. Colonoscopy, on the other hand, enables a finding of the colon area. Examination methods in the area of the small intestine are currently still unsatisfactory.

SUMMARY OF THE INVENTION

An object of the present invention is to provide a computer tomography apparatus that offers good examination possibilities for hollow organs, particularly in the area of the small intestine.

The object is achieved in accordance with the principles of the present invention in a computed tomography apparatus having a tiltable patient support, which supports a scan to be conducted with the patient in a substantially upright position and a substantially horizontal gantry, and having a control unit which, if the tiltable support is moved out of a precisely vertical alignment, causes the gantry to be moved by a corresponding angle out of a precisely horizontal position, so that the gantry and the patient support maintain the same angle relative to each other, such as a perpendicular angle, for all tilted positions of the patient support.

The examination of the intestinal region with contrast agent filling (for example, barium sulfate), as is currently standard in CT, is extremely difficult for a patient in suspine position since it is difficult to fill the intestine bubble-free in this position. Upright positioning of the patient and a horizontal alignment of the gantry avoid this disadvantage. A slight tilting of the table from the vertical positioning and a corresponding slope of the gantry can also be useful for better support of the patient. A tilt of the table and a tilting of the gantry that is clearly greater than currently standard (maximum±30%) is necessary in any case for the examination disclosed herein.

The actual examination is preceded by the production of an overview image for checking the distribution of the contrast agent.

Taking tomograms can be curried out in discreet steps or in a spiral (helical) mode. The spiral mode is preferred since shorter exposure times and fewer motion artifacts are expected in the spiral mode. Whether the patient is to be moved by the gantry or the gantry is to be moved over the patient for image acquisition does not represent a fundamental difference. Both techniques are possible and have been proposed for other examinations, for example lung examination. Regarding to the acquisition in the spiral mode, however, increased demands are made of the horizontal motion of the gantry or of the patient.

The upright support of the patient provides the diagnosing physician with an orientation in the proposed intestinal examination that is largely the same as in conventional fluoroscopy; a conventional fluoroscopic examination may precede the inventive examination.

The administration of contrast agent into the intestine is particularly advantageous for the following evaluations of the tomograms with the methods of three-dimensional surface reconstruction. Based on the reconstructed tomograms, the intestinal area is analyzed further with the 3-D method for the reconstruction of surfaces and secondary sections. As a result of filling the intestine with contrast agent, the intestine is distended (i.e., the cross section is spread) and a clear separation of the intestinal wall is enabled. A prerequisite is an optimally bubble-free filling of the intestine. If this is not always possible, then a good separation of the intestine can still also be achieved in the region of smaller air bubbles.

DESCRIPTION OF THE PREFERRED EMBODIMENTS

Figure 1:
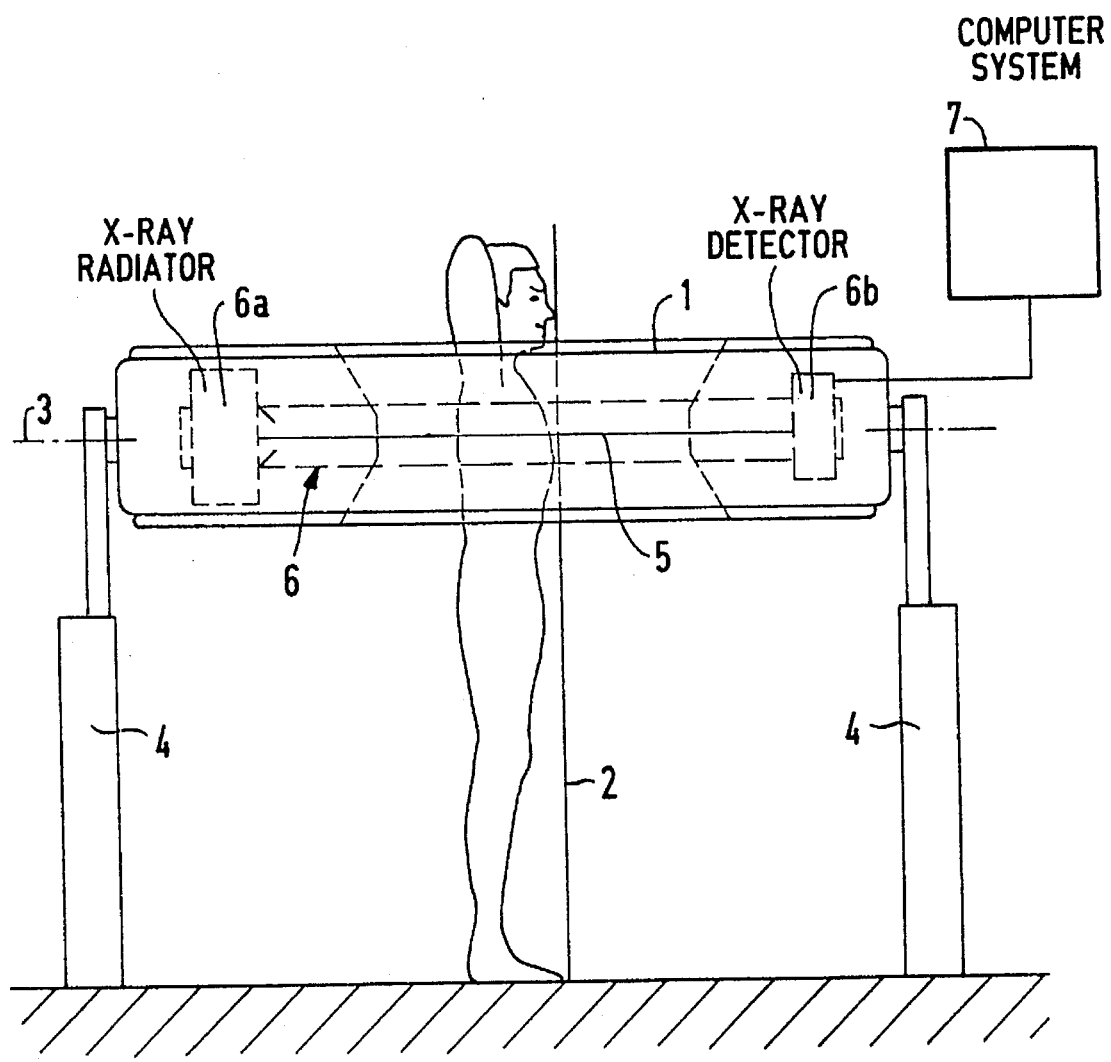
FIG. 1 shows the basic parts of a computed tomography apparatus for explaining the idea of the invention.

As shown in FIG. 1, the gantry 1 of a computed tomography apparatus together with the measurement system arranged therein is horizontally arranged, so that the patient can be examined while standing. The patient thereby supports himself against a supporting wall 2. The gantry 1 can be tilted around the horizontal axis 3 and is seated height-adjustable on supports 4. Given a standing patient, the gantry 1 is preferably operated in a horizontal position in order to obtain tomograms transversely relative to the body trunk. The respectively examined slice 5 is selected by setting the level of the gantry 1 in the vertical direction. When the gantry 1 is slowly, continuously adjusted in the vertical direction and the patient is thereby scanned with the rotating measurement system 6 composed of an x-ray radiator 6a and a detector 6b (measurement of the attenuation of the x-radiation by the body), then a spiral scan of a predetermined patient volume is obtained as in the case of a vertical gantry. The measured data are transmitted into the computer system 7 for further evaluation.

It is fundamentally of no significance when scanning the patient whether the gantry 1 is moved along the patient or the patient is moved through the gantry 1 with a height-adjustable device (for example, supporting wall 2 with a lift). For smoother support, and thus to reduce motion artifacts, however, a support slightly inclined relative to the perpendicular is advantageous. Various embodiments of the inclined support are possible.

Figure 2:
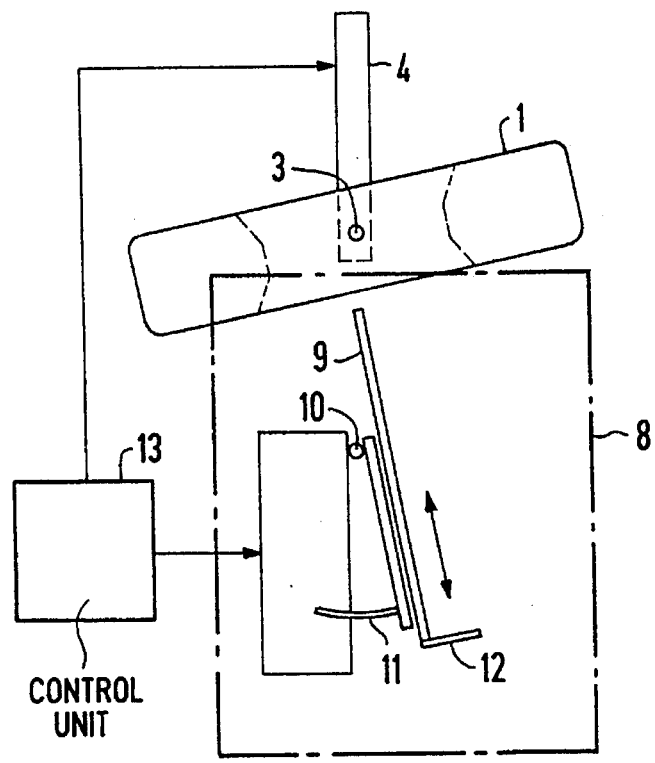
FIGS. 2 and 3 show details of the computer tomograph of FIG. 1 in accordance with the principles of the present invention.

FIG. 2 shows a support 8 having a moving, substantially perpendicularly oriented plate 9. The inclination of the plate 9 can be set by an articulation 10 and a tilt device 11. The patient moves through the gantry 1, set perpendicularly relative to the plate 9, on the plate 9 with a standing surface 12 integrated therein. The plate and gantry tilt are controlled by a control unit 13 such that the plate 9 and gantry 1 reside perpendicularly relative to one another at all times during a scan. Given a setting of the plate tilt, thus, the setting of the gantry 1 follows automatically. The setting of a constant inclination of the gantry 1 relative to the patient axis is likewise possible.

Figure 3:
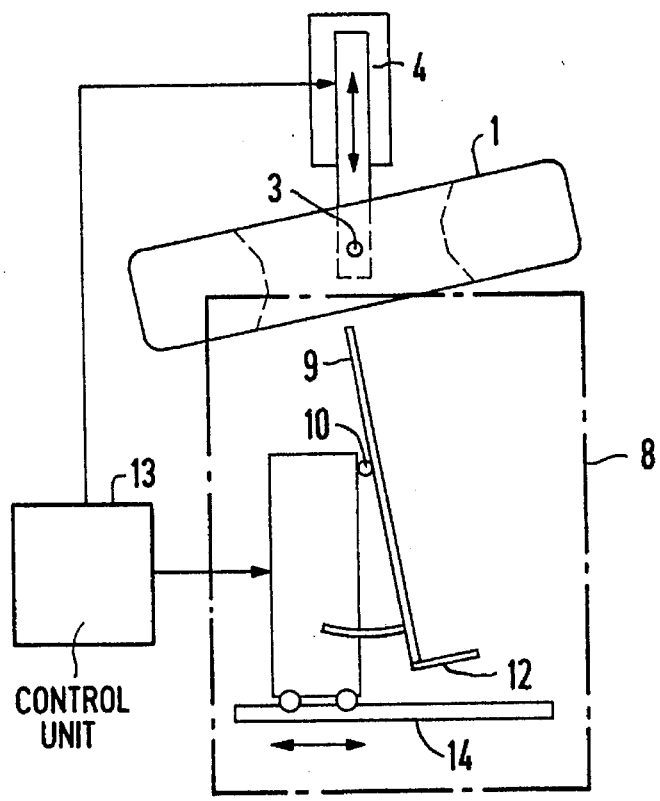

FIG. 3 shows a further possible embodiment. In this embodiment, the correspondingly inclined gantry 1 is moved in the vertical direction with the support 4 and the plate 9 is correspondingly moved in horizontal direction with the guide 14. The two movements are again controlled with the control unit 13 such that the patient moves perpendicularly relative to the gantry 1. In addition to the arrangement of FIG. 2, the control unit 13 operates so as to insure that the patient is located in the center of the gantry 1.

Figure 4:
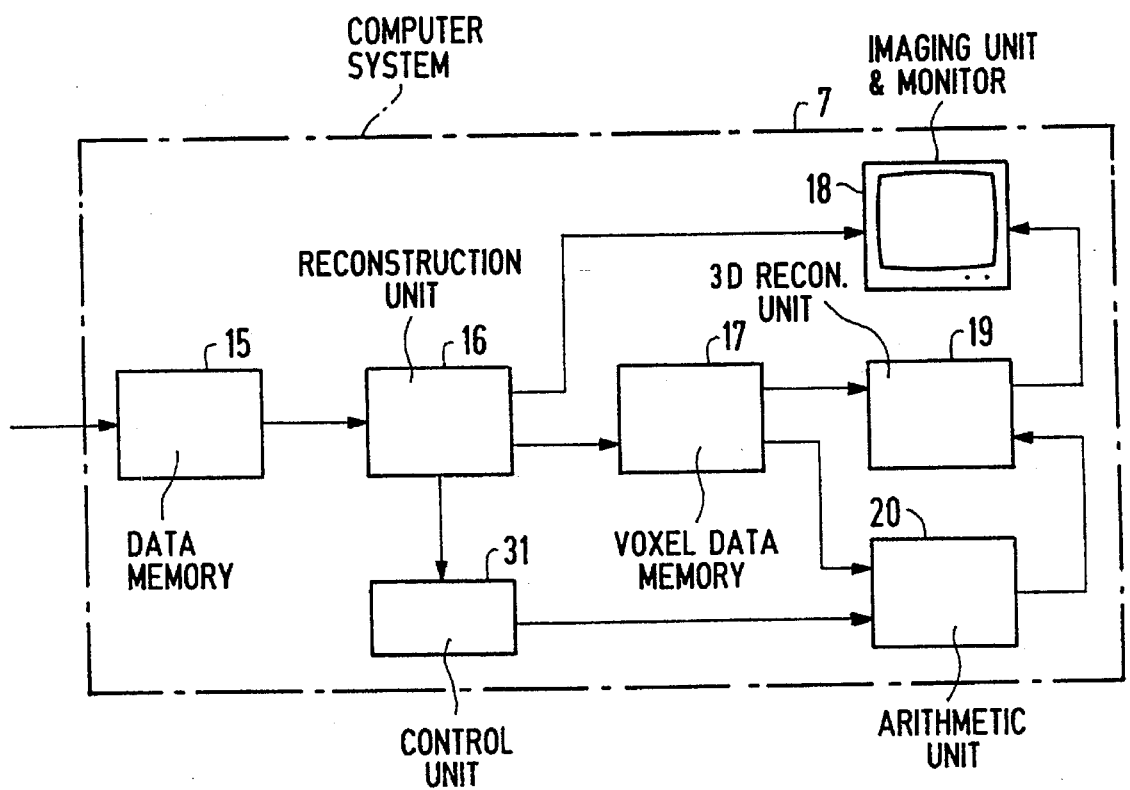
FIG. 4 is a block circuit diagram of the processing and image display circuit for the computed tomography apparatus of FIGS. 1—3.

The evaluation of the measured data is carried out with the computer system of FIG. 4. The data supplied from the gantry are intermediately stored in the measured data memory 15 and are subsequently processed with the reconstruction unit 16 to form transversal tomograms. The volume data (vexel elements) ordered according to slices are then deposited in the vexel data memory unit 17 as images for further processing. A display of the tomograms is simultaneously possible on the imaging unit with monitor 18 for supervision.

Figure 5:
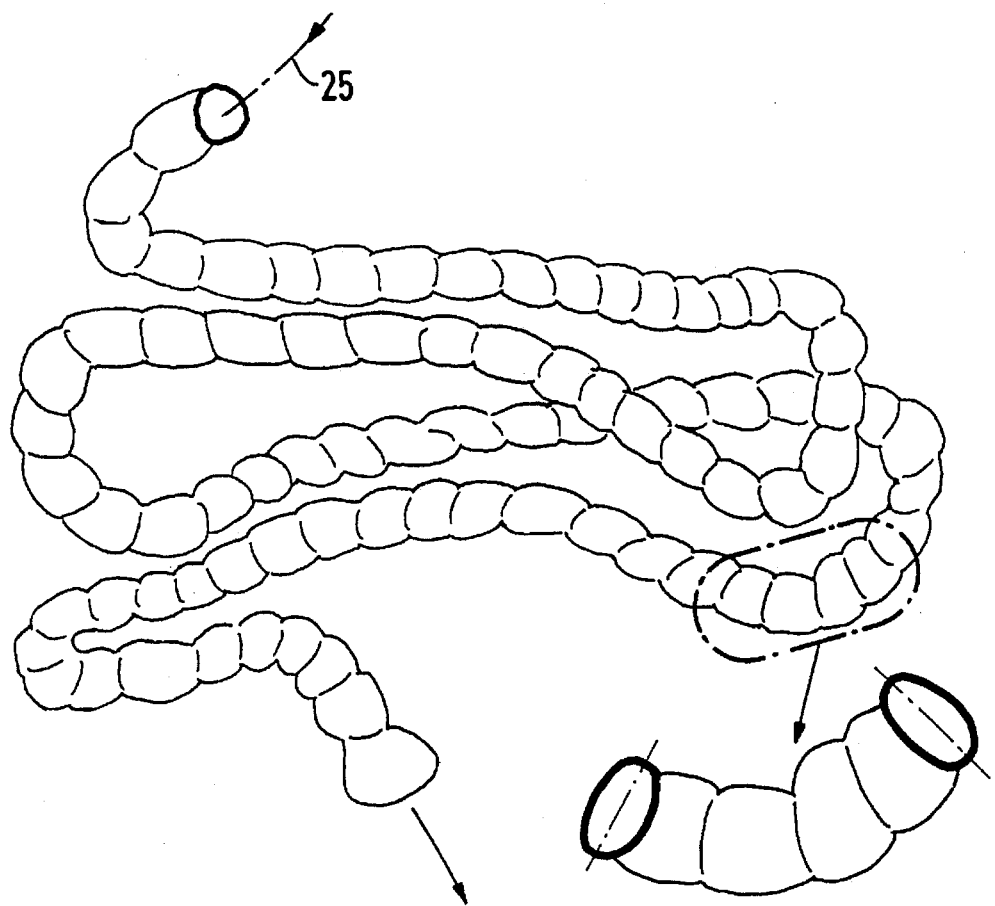
FIG. 5 is a schematic representation of a portion of the small intestine, for assisting in explaining an examination method useable in combination with the apparatus of FIGS. 1-4.

Examination of the intestinal region, especially the small intestine region, is extremely difficult with reference to the transversal slices because of the folded, convoluted arrangement of the intestine (see FIG. 5). Even standard, multiplanar secondary reconstructions provide only a limited view since only limited sub-regions respectively lie within the region of the slice.

The following method for evaluating the vexel data in accordance with the invention improves the presentation and achieves a simpler and more predictive finding.

Figure 6:
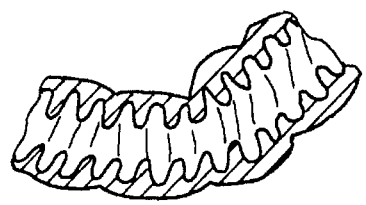
FIG. 6 is a schematic representation of the display of side-by-side halves of a section of the small intestine, achievable in the apparatus of the invention.
Figure 6:
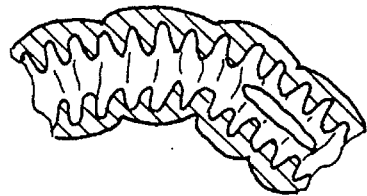

The contrast agent in the intestine can be imaged as a separate member, the contrast agent trunk. It can be presented with known methods of 3-D reconstruction proceeding from the vexel data of the tomograms. This contrast agent trunk is embedded in the intestine. When the image of the intestine is cut open over its length with the 3-D reconstruction and the contrast agent trunk is removed from the image of the intestine, then the inside of the intestine becomes visible by the computations of the unit 19 (FIG. 4) for the 3-D reconstruction. The two halves can be displayed side-by-side on the monitor 18 (with respect thereto, see FIG. 6 that shows the two halves for the excerpt in FIG. 5). Due to the folded arrangement of the intestine in the abdominal cavity, this presentation is also only possible in planar sections. An interactive operation with transversal tomograms 21 and the secondary section 22 orthogonal thereto is necessary for defining the individual sections (see FIG. 7).

Figure 8:
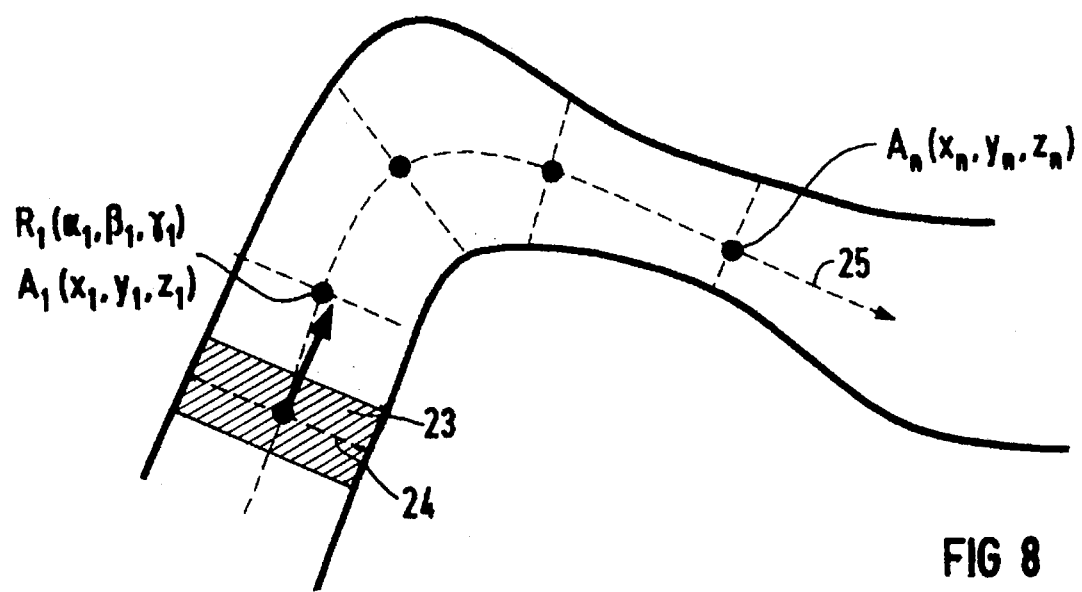
FIGS. 8, 9, 10 and 11 respectively illustrate a sequence of steps in method for obtaining a number of images of a portion of the small intestine implemented in the apparatus of the invention.

The definition of the individual sections is difficult and the diagnosis thereof is complicated at the region boundaries. An quick presentation and further assistance in the evaluation can be obtained on the basis of an automatic developed view, or involution of the intestine. To that end, it is necessary to evaluate the course of the intestine in the voxel data. The course of the intestine (see FIG. 8) is defined with a sequence of coordinate values A (x, y, z) in the three-dimensional space for the computer-assisted evaluation. The coordinates indicate the center of a small section 23 of intestine. The position of the cross sectional surface 24 through the center is identified by the direction R ($\alpha$, $\beta$, $\gamma$) perpendicular to the cross sectional area. The sequence of coordinate values $A_n$, or their connecting line, is referred to as the track 25 of the intestine in FIG. 8. A separate arithmetic unit 20 is provided in FIG. 4 for the complicated calculations required for identifying the track.

Figure 9:
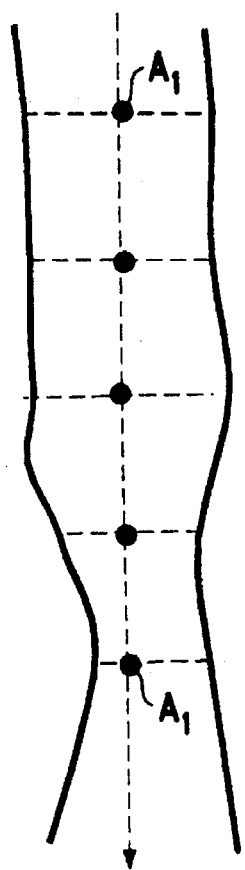

An entire involution of the interior view of the intestine is possible in elongated form (straight track) on the basis of the coordinate values and the directions of the cross sectional areas (FIG. 9). To this end, the individual cross sections are joined to one another and are connected on the basis of a corresponding interpolation of the original data. When this process is automated, the entire region can be displayed on the monitor 18 for the observer. A monitoring of the region to be displayed is possible with a graphic input (mouse or track ball) via the control arithmetic unit 31 (FIG. 4). It is thus also possible to move continuously forward and backward along the track 25 at an arbitrary speed.

If a critical location suspected of pathological modification is observed during the review, then a secondary cut plane can be calculated at this location perpendicularly relative to the intestine or an enlarged excerpt of the surface can be calculated with the unit 19 for a more detailed viewing. Automatic forwarding in secondary cut plane along the track 25 is likewise possible.

Methods for recognizing structures and for their tracking are known in the art. In medical technology, such known methods include, for example, methods for computer-assisted recognition and tracking of veins (vessel tracking) and nerves (nerve tracking).

Figure 12:
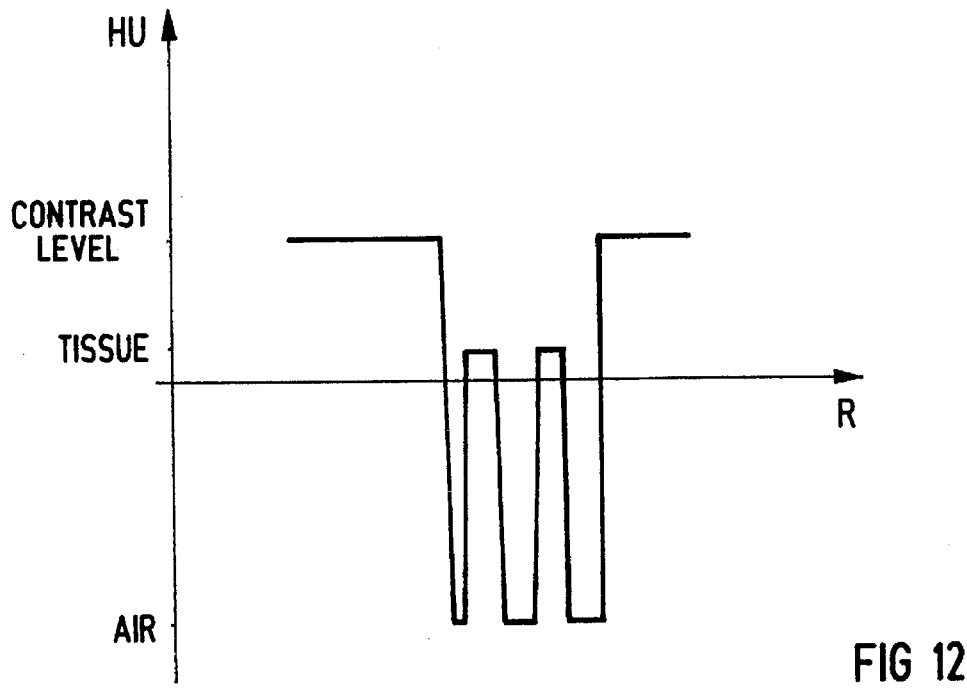
FIG. 12 is a graph showing the attenuation profile along a search line obtained in accordance with the method shown in FIGS. 8–11.

Due to the specific structure of the inside wall of the intestine with its ring-like interior projections and the frequent, tight bends of the small intestine, a specific method is proposed here for calculating the track 25 through the intestine or contrast agent trunk. A schematic illustration of a longitudinal cut through an intestinal section 26 with the valvulae conniventes (valves of Kerkring) 27 typical of the small intestine is shown in FIGS. 10–12 for describing the method.

Figure 7:
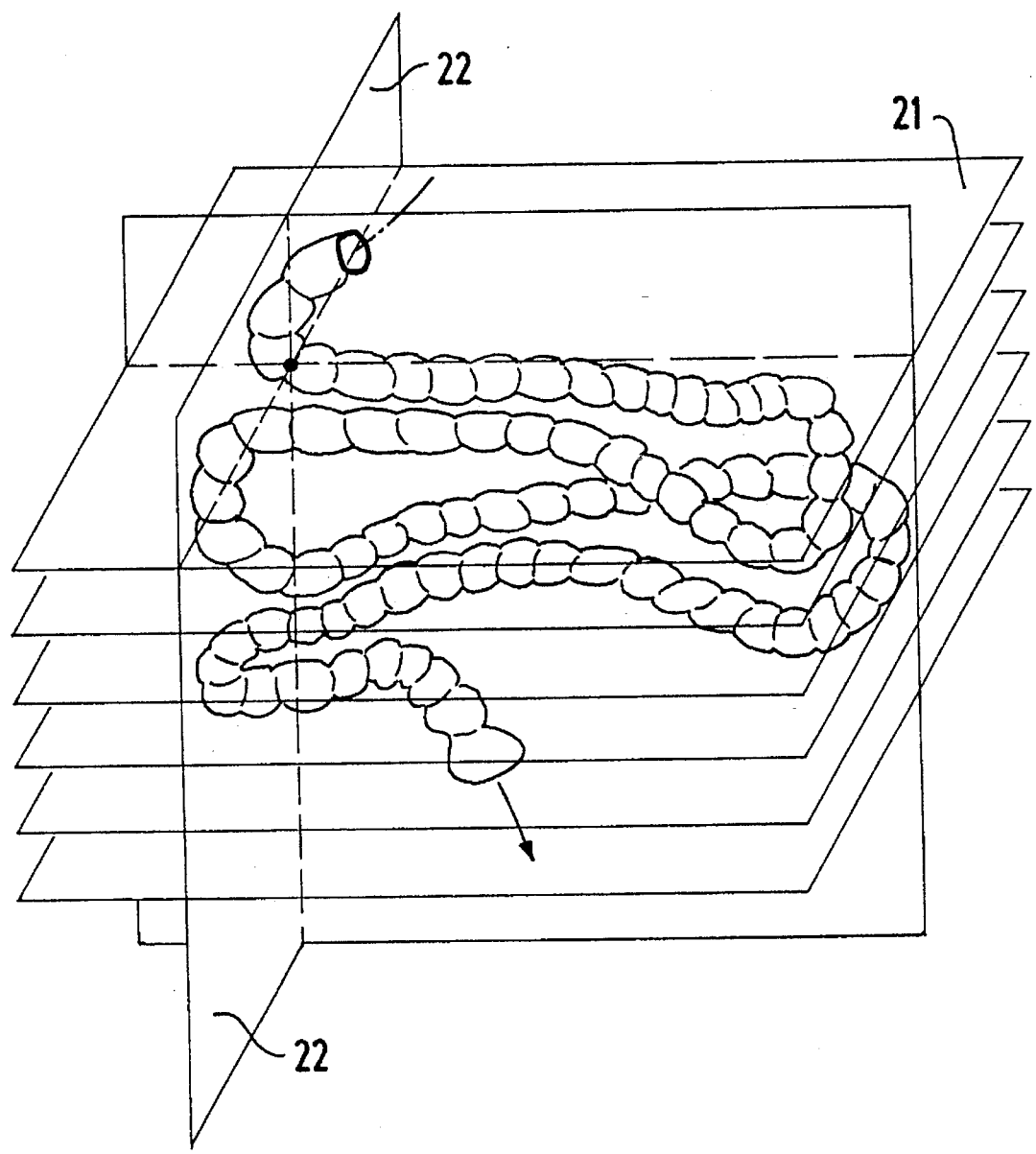
FIG. 7 illustrates a plurality of transversal tomograms of the small intestine obtainable with the apparatus of the invention.
Figure 10:
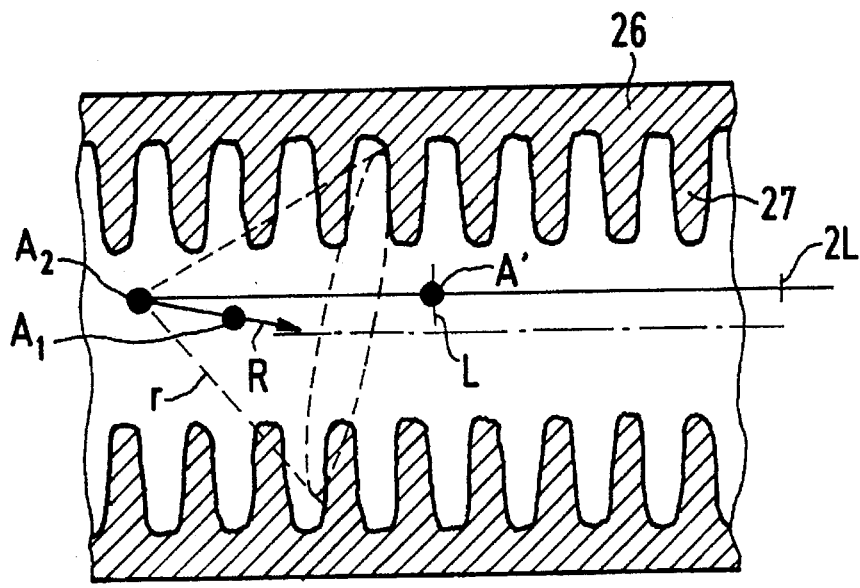
Figure 11:
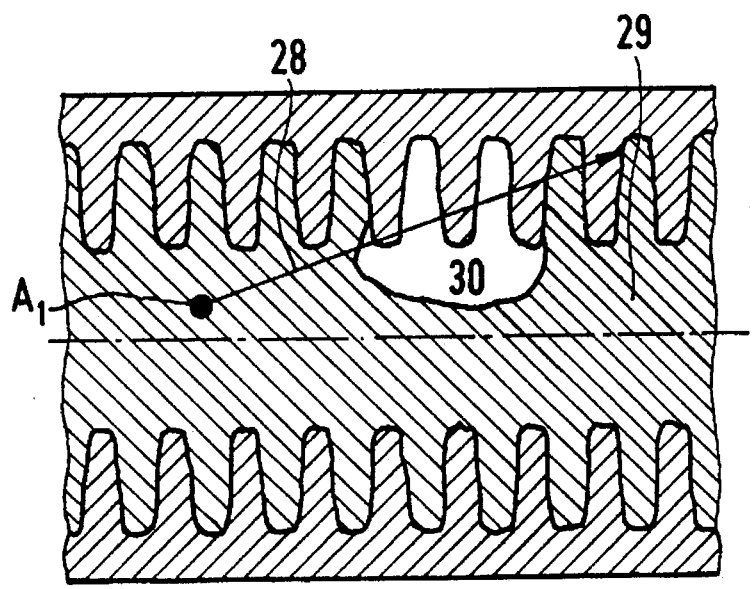

The calculation of the track 25 is implemented in a plurality of steps:

In a first step, a starting point A1 for the search path is defined using two orthogonal slices (see FIGS. 7, 10 and 11).

By selecting an additional point A2, the direction R in which the track is to be tracked at the beginning is defined. The calculation of the orthogonal slices again ensues in the unit 19. The input of the points ensues via the control unit 31. Correspondingly, a destination region for the track 25 is prescribed at the end of the intestine insofar as necessary. When the intestine ends at the edge of an image excerpt, then the edge is automatically the destination region.

Proceeding from the starting point A1, in a second step a search is made for an optimally long, free path distance in the inside of the intestine within a conical region defined by a central axis R and a solid angle r with respect thereto. The search line 28 thereby can move only in the contrast agent 29 or in air 30. The attenuation profile along an imaginary search line is shown in FIG. 12 (Houndsfield units (HU) v. intestinal length). One can see the clear limitation of intestine tissue (40–60 HU), contrast agent (>500 HU) and air ($\approx$–1000 HU). The end of the free search path is defined by the transition from contrast agent to tissue or from air to tissue. The individual regions are thus clearly separated with respect to the attenuation values. Due to the irregular edge structures of the tissue, however, averaging must always be undertaken over a small sub-volume of n by n by n voxels before the threshold decision (for example, n=3, . . . , 9). The employment of linear and non-linear, three-dimensional digital filters is possible for this purpose. The direction having the longest free search path is selected as the direction R' of the track in the next section.

In a third step, the length of the sub-section, or the spacing to the next starting point A' is selected. A maximum lengths of a sub-section L to be evaluated is prescribed in advance. When the free search path is then s>2L, then A' is defined at a spacing of L from A in the direction R', i.e. s'=L. When the path amounts to s<2L, then s'=s/2 is defined. In order to avoid a premature abort of the evaluation, an adaptation or matching of the solid angle r is also to be undertaken dependent on the length the maximum search path s, as set forth below. The second and third steps are then repeated until the track reaches an edge region of the image or ends in a previously prescribed destination region in accord with the first step.

The last step of the search procedure has thus been reached. The calculated track can be displayed as a projection in an orthogonal secondary cut plane for checking the procedure. A 3-D illustration of the track is likewise possible.

Figure 13:
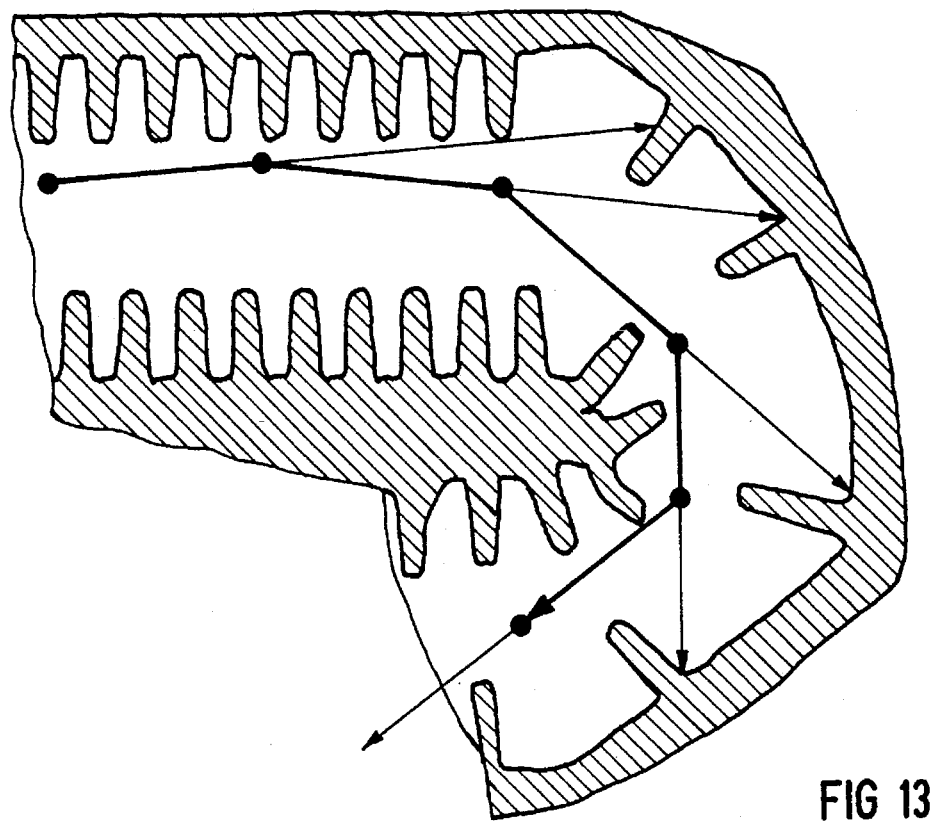
FIG. 13 illustrates the application of the method of FIGS. 8–11 to a portion of the small intestine having a significant curvature.

The described method for locating the track through the intestine is able also to traverse great curvatures according to FIG. 13. As a consequence of the uneven inside wall of the intestine, however, care must be exercised to insure that the method does not prematurely end in a dead-end. When, for example, the maximum search path s that has been found becomes smaller and smaller, this is an indication of a premature end of the track definition. On the basis of a simultaneous expansion of the solid angle r, an automatic reversing of the path direction can be achieved for leaving the dead-end. Tight, additional loops in the track can arise as a result of such detours, these being an impediment for the later unwinding of the intestine and for the examination of interest. A subsequent smoothing of the track and a method for recognizing superfluous loops as well as their elimination can follow the search process.

Figure 14:
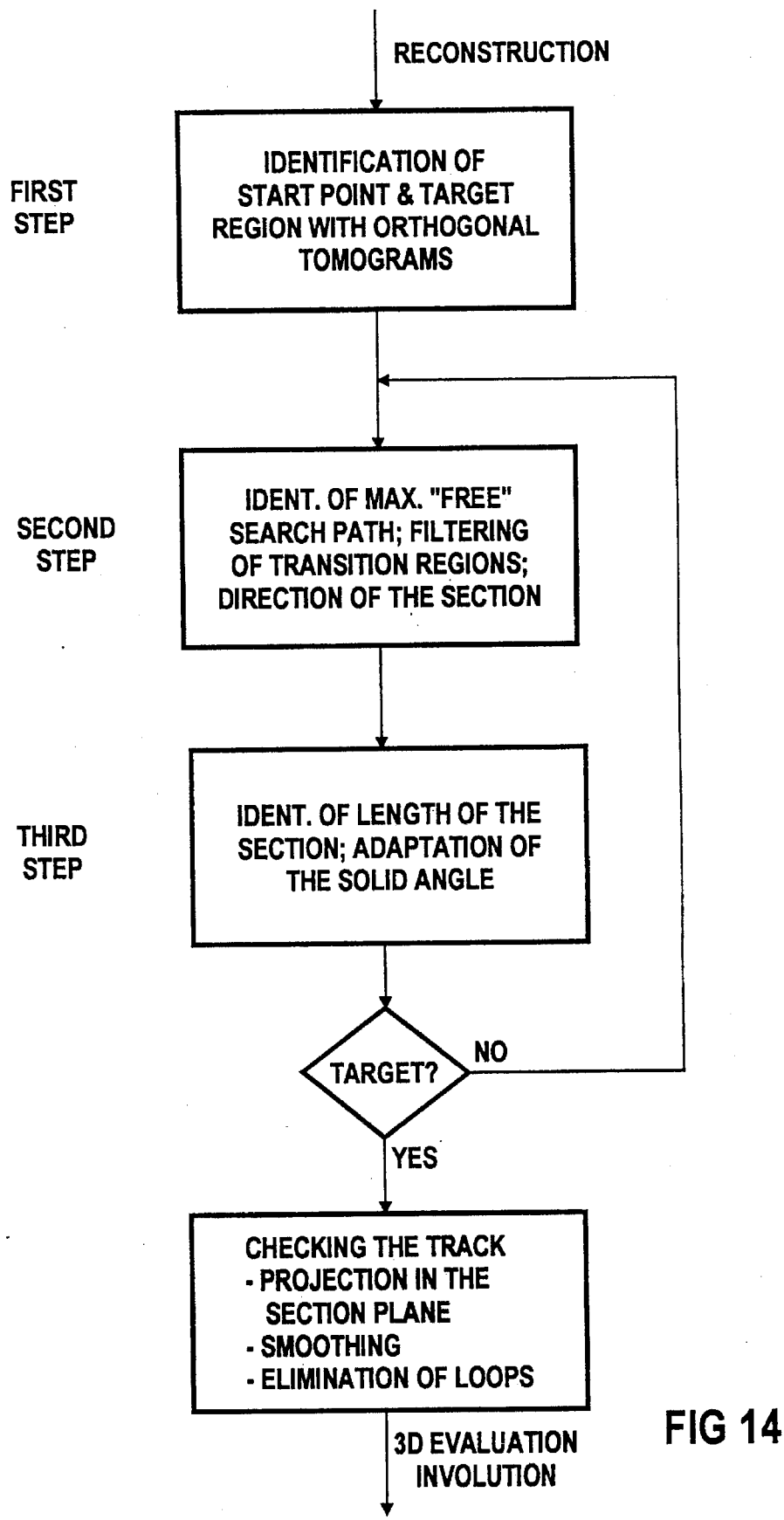
FIG. 14 is a flow chart setting forth the steps of the method illustrated in FIGS. 8–11.

The entire search process for the reconstruction of the track through the intestine region is summarized in FIG. 14 in a flowchart.

Due to the irregular tissue structures and the quantum noise that is always present, the method constitutes an optimization with unsharp limits. The identification of the maximum search path can thus also be implemented with the methods of fuzzy logic. Given a corresponding definition of the necessary parameters for the fuzzy process, one achieves an acceleration of the method.

The methods for presentation of the intestinal region presented in the embodiments can be realized both with the specific calculating units of FIG. 4 as set forth and can also be realized with a suitable computer having an appropriate computing capacity. The function units are then to be realized as sub-programs on the computer.

Although modifications and changes may be suggested by those skilled in the art, it is the intention of the inventors to embody within the patent warranted hereon all changes and modifications as reasonably and properly come within the scope of their contribution to the art.

I claim as my invention:

1. A computed tomography apparatus for examining hollow organs in an examination subject, comprising:

patient support means for supporting an examination subject having a torso and a mid-section in a standing upright position relative to a vertical axis;

a gantry containing an x-ray source and an x-ray detector and having an opening therein between said x-ray source and said x-ray detector for surrounding an entirety of said examination subject, said gantry being oriented at an angle relative to a horizontal axis and said patient support means and said gantry being relatively oriented for permitting movement of said gantry along the torso and the mid-section while the patient is in said standing upright position on said patient support means;

means for producing relative movement between said examination subject and said gantry to conduct a scan of a region of said examination subject contained within the torso and mid-section while rotating said x-ray source and said x-ray detector around said subject to obtain a plurality of sets of attenuation data;

computer means for processing said attenuation data to generate and display a plurality of tomograms of said examination subject; and control means for tilting said patient support means relative to said vertical axis and for displacing said gantry relative to said vertical axis for maintaining a constant angle between said gantry and said patient support means for every position of said patient support means.

2. A computed tomography apparatus as claimed in claim 1 wherein said patient support means comprises said means for relatively moving said examination subject and said gantry by conveying said examination subject through said opening in said gantry during said scan with said gantry at a selected tilt angle relative to said vertical axis.

3. A computed tomography apparatus as claimed in claim 1 wherein said means for relatively moving said examination subject and said gantry comprises means for simultaneously moving said gantry and said patient support means for conveying said examination subject through said opening in said gantry at a selected tilt angle relative to said vertical axis.

4. A computed tomography apparatus as claimed in claim 1 wherein said control means comprises means for maintaining said gantry and said patient support means perpendicularly relative to each other for every position of said patient support means.

5. A computed tomography apparatus as claimed in claim 1 wherein said gantry has a center disposed in said opening, and wherein said control means comprises means for simultaneously horizontally controlling positioning of said patient support means and vertically controlling positioning of said gantry for maintaining said examination subject at said center of said gantry during said scan.

6. A computed tomography apparatus as claimed in claim 1 wherein said computer means comprises arithmetic means for three-dimensional image reconstruction from said image data reconstructed from said attenuation data by computationally slicing a hollow organ filled with contrast agent in said examination subject to produce a contrast agent trunk and for computationally removing and displaying said contrast agent trunk from an interior of said hollow organ.

7. A computed tomography apparatus as claimed in claim 1 wherein said computer means comprises means for displaying tomographic image of said examination subject containing an organ which is computationally sliced into halves and for displaying said halves side-by-side.

8. A computed tomography apparatus as claimed in claim 1 wherein said computer means comprises means for computationally generating an involution of an interior view of a hollow organ of said examination subject and for displaying said involution by distortion correction and interpolation.

9. A computed tomography apparatus as claimed in claim 8 wherein said computer means comprises means for identifying a length and direction of a maximum free search path in said hollow organ by fuzzy logic.

10. A computed tomography apparatus as claimed in claim 1 wherein said computer means comprises arithmetic means for identifying a track through said hollow organ.

* * * * *